United States Patent [19]

Hommeltoft

[11] Patent Number: 5,618,769
[45] Date of Patent: Apr. 8, 1997

[54] PROCESS FOR THE RECOVERY OF ALKYLATION CATALYST

[75] Inventor: Sven I. Hommeltoft, Hillerod, Denmark

[73] Assignee: Haldor Topsøe A/S, Denmark

[21] Appl. No.: 400,859

[22] Filed: Mar. 8, 1995

[30] Foreign Application Priority Data

Mar. 10, 1994 [DK] Denmark .................................. 0278/94

[51] Int. Cl.$^6$ ........................... B01G 38/60; B01G 38/66
[52] U.S. Cl. ................................. 502/26; 502/27
[58] Field of Search .......................... 502/26, 27

[56] References Cited

U.S. PATENT DOCUMENTS

| 5,264,649 | 11/1993 | Eastman et al. | 585/802 |
| 5,306,859 | 4/1994 | Eastman et al. | 585/724 |

FOREIGN PATENT DOCUMENTS

| 0433954 | 6/1991 | European Pat. Off. | C07C 2/62 |

Primary Examiner—Helane Myers
Assistant Examiner—Alexander G. Ghyka
Attorney, Agent, or Firm—Ostrolenk, Faber, Gerb & Soffen, LLP

[57] ABSTRACT

Process for the recovery of spent fluorinated sulfonic catalyst from acid soluble oil (ASO) being formed during alkylation of hydrocarbons in the presence of the acid catalyst. The process includes washing the ASO with water and recovering an aqueous solution of the acid catalyst, neutralizing the acid in the aqueous solution by adding to the solution a basic compound being selected from the group of amino compounds, ammonia and ammonium salts, thereby, forming ammonium salts of the acid catalyst with a melting point at which the obtained acid catalyst salt in a subsequent concentration and drying step is in the form of a melt, drying the melt, and finally recovering the acid catalyst by protonization of the dried melt with sulfuric acid and distilling off the recovered acid catalyst from the sulfuric acid.

4 Claims, No Drawings

PROCESS FOR THE RECOVERY OF ALKYLATION CATALYST

BACKGROUND OF THE INVENTION

1. Field of the Invention

The present invention is directed to certain improvements in the alkylation of aliphatic hydrocarbons in the presence of a fluorinated sulfonic acid catalyst.

More particularly, the invention is related to the recovery of the fluorinated sulfonic acid catalyst acid soluble oil (ASO) in the form of a tar from being formed as byproduct during alkylation of hydrocarbons.

2. Description of the Related Art

Acid catalyzed alkylation of aliphatic hydrocarbons with olefinic hydrocarbons is a well known process for the preparation of high octane gasoline products. Alkylation of aliphatic hydrocarbons is generally accomplished in the liquid phase by reacting paraffins and olefins in the presence of a strong acid catalyst.

Utilization of fluorinated sulfonic acids as efficient alkylation catalysts in the alkylation of aliphatic hydrocarbons with olefins, is disclosed in European Patent Application No. 433,954, which by reference is incorporated herein. By the disclosed process, a process stream including a hydrocarbon substrate and an olefinic alkylating agent is reacted by contact with the fluorinated sulfonic acid catalyst in a fixed bed alkylation reactor containing polar contact material. On the contact material is established a reaction zone with the fluorinated sulfonic acid catalyst adsorbed within a confined area of the contact material. In the reaction zone, the process stream is converted at alkylating conditions to a product stream of alkylated hydrocarbons by catalysis of the fluorinated sulfonic acid.

During the alkylation reaction, the acid catalyst and, consequently, the reaction zone moves as a well-defined band between the ends of the reactor due to interaction with the process stream flowing through and reacting in the zone.

During migration of the acid catalyst on the contact material, the catalytic activity of the fluorinated sulfonic acid is substantially retained and the acid is still catalytic active when the reaction zone reaches the reactor outlet.

Although it is possible to reuse the acid catalyst, as it reaches the outlet end of the alkylation reactor by reversing the flow direction of the process stream introduced into the alkylation reactor, small amounts of the acid catalyst will continuously be trapped in ASO byproduct being formed by side reactions during the process. The ASO adsorbs like the acid catalyst as a movable band on the support material adjacent to the reaction zone. It is, thus, possible to withdraw the ASO from the reactor, whenever it reaches one of the ends of the reactor.

Even if the ASO contains only small amounts of spent acid catalyst, it is desirable to recover the catalyst from the ASO in order to improve the economy of the alkylation process. Conventional methods, like distillation or extraction of the acid directly from the ASO, are not efficient because of strong interaction between the sulfonic acid and basic components in the tar.

It is, therefore, a principal object of this invention to provide a process for the efficient recovery of fluorinated sulfonic acid catalyst from an alkylation process.

In DK patent application No. 0287/93 a recovery process is disclosed, in which spent fluorinated sulfonic acid catalyst is regained by stepwise treating ASO from an alkylation process containing spent catalyst with a proton donating acid to convert the catalyst to its free acid form, and then removing the acid by stripping the tar with an inert stripping agent.

Spent fluorinated sulfonic acid catalyst may quantitatively be recovered by extracting the catalyst containing ASO with water. After extraction with water, it has been shown that the content of fluorinated sulfonic acid catalyst in the extracted ASO is below one ppm. Extracted acid catalyst can be recovered from the aqueous solution by neutralization with a base, and, subsequently, protonization in sulfuric acid and distillation of the acid.

A substantial quantitative recovery is thereby provided.

The above process provides an efficient recovery of valuable fluorinated sulfonic acid catalyst. The recovery of the acid after neutralization with a base, however, represents certain problems; thus, a number of steps in the further treatment of the obtained salt from the neutralization step, in particular, drying of the salt, complicates the recovery process and diminishes the overall process economy.

SUMMARY OF THE INVENTION

It has now been found that the above disadvantages during drying of recovered acid catalyst salt during recovery of spent alkylation acid catalyst can be avoided by addition of ammonia or organic amino compounds to an aqueous extract of acid containing ASO, whereby salts of the acid catalyst are formed having a melting point at which the salts can be treated in subsequent recovery steps in the liquid phase.

According to the above observation, this invention provides a process for the recovery of spent fluorinated sulfonic acid catalyst from ASO being formed during alkylation of hydrocarbons in the presence of the acid catalyst, comprising steps of washing the tar with water and recovering an aqueous phase of the acid catalyst, adding a basic compound being selected from the group of organic amino compounds, ammonia and ammonium salts and, thereby, forming ammonium salts of the acid catalyst, having a melting point at which the recovered acid catalyst salt in a subsequent concentration and drying step is in the form of a melt, and finally recovering the acid catalyst by protonization of the dried melt with sulfuric acid and distillation of the recovered acid catalyst from the sulfuric acid.

After recovery of the acid catalyst by distilling off the protonated acid catalyst from sulfuric acid, used amino compounds may be recovered by ion exchange with ammonium salt solutions or ammonia.

When employing ammonia during the recovery process for the formation of ammonium salts, those salts may have an inconvenient, high melting point depending on the actual acid catalyst to be recovered. In order to decrease the melting point of the ammonium salts, it is preferred to admix ammonium hydrogen sulfate or alkylammonium hydrogen sulfate, which results in a mixture of salts with a melting point being in the appropriate range for subsequent treatment. The obtained salt mixtures are then dried in the form of a melt in the liquid phase.

DETAILED DESCRIPTION OF THE PREFERRED EMBODIMENTS

The above features of the invention will further be illustrated in the following Example.

EXAMPLE

Extraction of trifluoromethanesulfonic acid catalyst from ASO.

1790 g acid containing ASO were poured over 2 liters crushed ice.

Thereby, an aqueous phase with the acid catalyst was separated from an oil phase. The oil phase was washed once with water, dried over sodium sulfate and analyzed for trifluoromethanesulfonic acid salts after boiling in ammonia water by ion-chromatographic analysis. The content of acid catalyst was below the detection limit of 0.5 ppm in the oil phase.

The trifluoromethanesulfonic acid retained in the aqueous phase was recovered by neutralization through addition of trimethylamine or triethylamine resulting in a solution of the respective ammonium salts. The melting point of the ammonium salts was:

$Et_3NH^+TfO^-$ (Triethylammoniumtriflate) : 41° C., $Me_3NH^+TfO^-$ (Trimethylammoniumtriflate) : 140° C.

25.1 g (0.10 mole) $Et_3NH^+TfO^-$ were mixed with 25 ml 99.9% sulfuric acid and distilled at 11 mm Hg in a 20 cm Vigreaux column. 14.5 g trifluoromethanesulfonic acid were recovered at 56°–60° C. giving a recovery of 97%. The remaining 3% of the acid was found in the sulfuric acid residue.

20.9 g (0.10 mole) $Me_3NH^+TfO^-$ were treated with 25 ml 99.9% sulfuric acid and distilled at 10 mm Hg in a similar manner as with the triethylammonium salt. At 50°–56° C., 15.35 g of a distillate containing 86% trifluoromethanesulfonic acid were obtained corresponding to 13.3 g trifluoromethanesulfonic acid at 89% recovery.

I claim:

1. Process for the recovery of spent fluorinated sulfonic catalyst from acid soluble oil (ASO) being formed during alkylation of hydrocarbons in the presence of the acid catalyst, comprising the steps of:

washing the ASO with water and recovering an aqueous solution of the acid catalyst;

neutralizing the acid in the aqueous solution by adding to the solution a basic compound being selected from the group consisting of amino compounds, ammonia and ammonium salts to obtain ammonium salts of the acid catalyst, the obtained acid catalyst salts having a melting point;

forming a melt of the obtained acid catalyst salts;

drying the acid catalyst salts in the form of the melt to obtain a dried melt; and recovering the acid catalyst by protonization of the dried melt with sulfuric acid and distilling off the recovered acid catalyst from the sulfuric acid.

2. The process of claim 1, wherein the amino compounds used in the neutralization step comprises methyl and/or ethylamino compounds.

3. The process of claim 1, wherein the melting point of the obtained acid catalyst salts is further decreased by addition of ammonium hydrogen sulfate.

4. The process of claim 1, wherein the melting point of the obtained acid catalyst salts is further decreased by addition of alkylammonium hydrogen sulfate with the general formula:

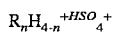

where n is between 1 and 3 and R is an alkyl group.

* * * * *